(12) United States Patent
Antonini

(10) Patent No.: US 7,692,013 B2
(45) Date of Patent: Apr. 6, 2010

(54) METHOD FOR SEPARATION AND PURIFICATION OF HYDROCODONE BY PREPARATIVE CHROMATOGRAPHY

(75) Inventor: Enrico A. Antonini, Edwardsville, IL (US)

(73) Assignee: Mallinkrodt Inc., Hazelwood, MO (US)

( * ) Notice: Subject to any disclaimer, the term of this patent is extended or adjusted under 35 U.S.C. 154(b) by 0 days.

(21) Appl. No.: 11/576,059

(22) PCT Filed: Oct. 26, 2005

(86) PCT No.: PCT/US2005/038603

§ 371 (c)(1),
(2), (4) Date: Mar. 27, 2007

(87) PCT Pub. No.: WO2006/052456

PCT Pub. Date: May 18, 2006

(65) Prior Publication Data

US 2007/0293676 A1 Dec. 20, 2007

Related U.S. Application Data

(60) Provisional application No. 60/622,430, filed on Oct. 27, 2004.

(51) Int. Cl.
*C07D 489/02* (2006.01)
(52) U.S. Cl. ............................................. 546/45
(58) Field of Classification Search ................. 549/457; 546/45
See application file for complete search history.

(56) References Cited

U.S. PATENT DOCUMENTS

| | | | |
|---|---|---|---|
| 2,715,626 | A | 8/1955 | Pfister et al. |
| 4,241,065 | A | 12/1980 | Boswell, Jr. et al. |
| 5,610,283 | A | 3/1997 | Buechler |
| 5,677,279 | A | 10/1997 | Young |
| 5,885,999 | A | 3/1999 | Elliott et al. |
| 5,981,751 | A | 11/1999 | Mudryk et al. |
| 6,136,824 | A | 10/2000 | MacLeod et al. |
| 6,359,111 | B1 | 3/2002 | Meyer et al. |
| 6,500,840 | B2 | 12/2002 | Myers et al. |
| 2002/0100727 | A1 | 8/2002 | Corcoran |
| 2004/0029888 | A1 | 2/2004 | Nilsson et al. |
| 2005/0113401 | A1 * | 5/2005 | Lawson ....................... 514/282 |

FOREIGN PATENT DOCUMENTS

WO    WO 03/074526    9/2003

OTHER PUBLICATIONS

Trauner et al., J. Org. Chem., 1998, 63(17), 5908-5918.*
Clement et al., Protein Expression and Purification, vol. 44, 2005, pp. 110-120.*
Soni et al., Separation of Standard Opiates and Their Analysis in Pharmaceutical and Illicit Preparations by Paired-Ion Reverse-Phase High Pressure Liquid Chromatography, Journal of Forensic Sciences, 1979, vol. 24, pp. 437-447, XP008060065.
Dams et al., Simultaneous determination of in total 17 opium alkaloids and opioids in blood and ruine by fast liquid chromatography-diodearray detection-fluorescence detection, after solid-phase extraction, Journal of chromatography B, 2002, 773, pp. 53-61.
Chen et al., Simultaneous determination of hydrocodone and hydromorphone in human plasma by liquid chromatography with tandem mass spectrometric detection, Journal of chromatography B, 2002, 769, pp. 55-64.
Dams et al., Comparison of phenyl-type columns in the development of a fast liquid chromatographic system for eighteen opiates commonly found in forensic toxicology, Journal of Chromatography A, 2000, 896, pp. 311-319.
Achilli, et al., Determination of illicit drugs and related substances by high-performance liquid chromatography with an electrochemical coulometric-array detector, Journal of Chromatography A, 1996, 729, pp. 273-277.
Gergely, A review of the application of chiroptical methods to analytical chemistry, Journal of Pharmaceutical & Biomedical Analysis, 1989, 7, No. 5, pp. 523-541.
Black et al., Isolation and identification of hydrocodone in narcotic cough by high=performance liquid chromatography with infrared sp metric identification, Journal of Chromatography, 1986, 358, pp. 438-443.

* cited by examiner

*Primary Examiner*—D. Margaret Seaman
*Assistant Examiner*—Niloofar Rahmani

(57) ABSTRACT

A process for the purification of an impure preparation containing hydrocodone by means of a reverse phase preparative chromatography process is provided. In an illustrative embodiment a chromatographic column is loaded with a stationary phase, typically a silica particle having an organic ligand bound thereto. The impure preparation is acidified and passed through the column with a loading ratio of from about 10 to about 1000. The column is eluted, typically with an aqueous solution of acetonitrile, and the purified hydrocodone is obtained in a specified fraction.

28 Claims, 2 Drawing Sheets

METHOD FOR SEPARATION AND PURIFICATION OF HYDROCODONE BY PREPARATIVE CHROMATOGRAPHY

CROSS REFERENCE TO RELATED APPLICATIONS

This application is a national stage application of PCT/US2005/038603, filed Oct. 26, 2005, which claims the benefit of U.S. Provisional Application No. 60/622,430 filed Oct. 27, 2004.

FIELD OF THE INVENTION

This invention relates to a method for the separation and purification of hydrocodone by means of reverse phase preparative chromatography. More particularly, the process of this invention economically provides highly pure hydrocodone in industrial quantities.

BACKGROUND OF THE INVENTION

Hydrocodone, also known as dihydrocodeinone or dicodide, is chemically 4,5-epoxy-3-methoxy-17-methyl-morphinan-6-one, CAS RN 125-29-1. The synthesis of hydrocodone and its pharmaceutically acceptable acid addition salts are described in U.S. Pat. No. 2,715,626 issued to Pfister et al, and in the Merck Index, 11th Edition, page 757, entry 4708 (1989). Hydrocodone is a narcotic antitussive and analgesic. At antitussive doses, hydrocodone also exerts analgesic effects. Hydrocodone exhibits a complex pattern of metabolism including O-demethylation, N-demethylation and 6-keto reduction to the corresponding 6-β-hydroxy metabolites.

Current processes result in a level of impurities, including α,β unsaturated ketones, that may not be optimal for commercial application. Thus, there is a need for a more efficient and direct method to isolate highly pure hydrocodone, especially when producing industrial quantities.

Means to achieve separation or purification of pharmaceuticals include adsorption processes such as the use of carbon. Unfortunately, the carbon irreversibly adsorbs the pharmaceutical of interest in addition to removing color and other unwanted substances. This creates a significant yield loss. In some instances, multiple precipitations are required in order to achieve the desired purity. This greatly increases the complexity of the process since the supernatant streams must be recycled for recovery. These additional precipitations also require using a greater volume of hydrocodone in the process with longer cycle times. Furthermore, the precipitation process can be lengthy in addition to the time that is sometimes required for heating and cooling. Also, some precipitations require extended filtration time due to the particle size of the product that is eventually produced.

Other drawbacks to the current process of purifying hydrocodone include a multiple of manual solid handling operations to recover the alkaloid or bitartrate salt. These operations lead to greater operator exposure to the hydrocodone with the associated reliance on engineering controls and personal protective equipment. This operation can be monotonous as well as tedious.

Another approach to purify hydrocodone is the use of adsorption through ion exchange. Although this has been done with alkaloids such as codeine and morphine, it has the limitation of requiring a low feed concentration. This is due to the need for the use of high pH flushes that can cause precipitation. Any precipitation can potentially compromise the entire column containing ion-exchange resin. Another disadvantage to this process is that significant salt is required so that another step of either dialysis or reverse osmosis is required for ion-removal.

Yet another way to achieve adsorption is through polar interaction or normal phase adsorption. Although this method is successful, it requires the extensive use of organic solvents. Moreover, although the hydrocodone could be purified in this manner, more evaporation would be required.

Any use of analytical chromatography on narcotics such as hydrocodone would guide an individual of ordinary skill in the art away from using preparative chromatography for an industrial scale process. Unlike preparative chromatography, analytical chromatography generally requires complete separation of each peak. The edition of the component peaks is measured often through the absorbance of ultraviolet (UV) light. In analytical chromatography the peak separation is achieved by loading an infinitely small mass of the feed onto the column, and using a small particle size diameter (often less than 5 micrometers in the stationary phase.) The small particle size generates much higher pressures than those found in preparative chromatography. These higher pressures mandate the use of very large, strong and expensive chromatography equipment, which would negate the commercial viability for this analytical process. The equipment would also be very large in consideration that an infinitely small mass of feed is loaded in each run. In preparative chromatography, the objective is to recover the desired feed component with the required purity. The desired component can be recovered with impurities, so long as the impurities are within specification limits. The particle size of the stationary phase is small enough to achieve the separation, but is often greater than 10 microns. This limits the pressure drop generated. Also, in preparative chromatography, the maximum amount of feed is loaded with the constraint of attaining the desired product quality. This allows the product to leave the column with a maximum concentration, which thereby minimizes the size of the downstream equipment, especially the evaporating or concentrating units.

The separation or purification of organics by means of the chromatographic processes is well known in the art. However, the materials separated by means of the chromatographic processes are greatly dissimilar to the present objects of this invention, i.e. the industrial scale separation and purification of hydrocodone. While there are numerous references to analytical chromatographic applications for hydrocodone, there is no suggestion that an industrial process could be employed under any conditions.

The present invention is directed to overcoming one or more of the deficiencies set forth above. These deficiencies include, but are not limited to, product yield loss, tedious manual solid handling operations such as the loading and unloading of centrifuges or filters, reliance on protective equipment by the operator, extensive processing steps and potential multiple precipitation in order to achieve the requisite purity requirements.

SUMMARY OF THE INVENTION

In one aspect of the present invention there is provided a process for recovering highly pure hydrocodone from an impure hydrocodone preparation. The process comprises subjecting the impure hydrocodone preparation to reverse-phase liquid chromatography wherein the loading ratio of a stationary phase to the hydrocodone is not more than about 1000, and wherein the highly pure hydrocodone recovered is at least about 95% pure.

In another aspect of the present invention there is provided a process for recovering highly pure hydrocodone from an impure preparation. The process comprises subjecting the impure preparation to a reverse-phase high performance preparative liquid chromatography and recovering highly pure hydrocodone.

In yet another aspect of the present invention there is provided a process for purifying an impure hydrocodone preparation containing an α,β unsaturated ketone. The process comprises the steps of packing a chromatographic column with a chromatographic packing material; passing an aqueous, acidified solution of hydrocodone preparation through the column at a loading ratio of from about 10 to about 1000; and eluting the column with an aqueous solution of an organic solvent to produce an eluate containing hydrocodone having less than 10 ppm α,β unsaturated ketone.

DETAILED DESCRIPTION OF THE INVENTION

Figure 1:
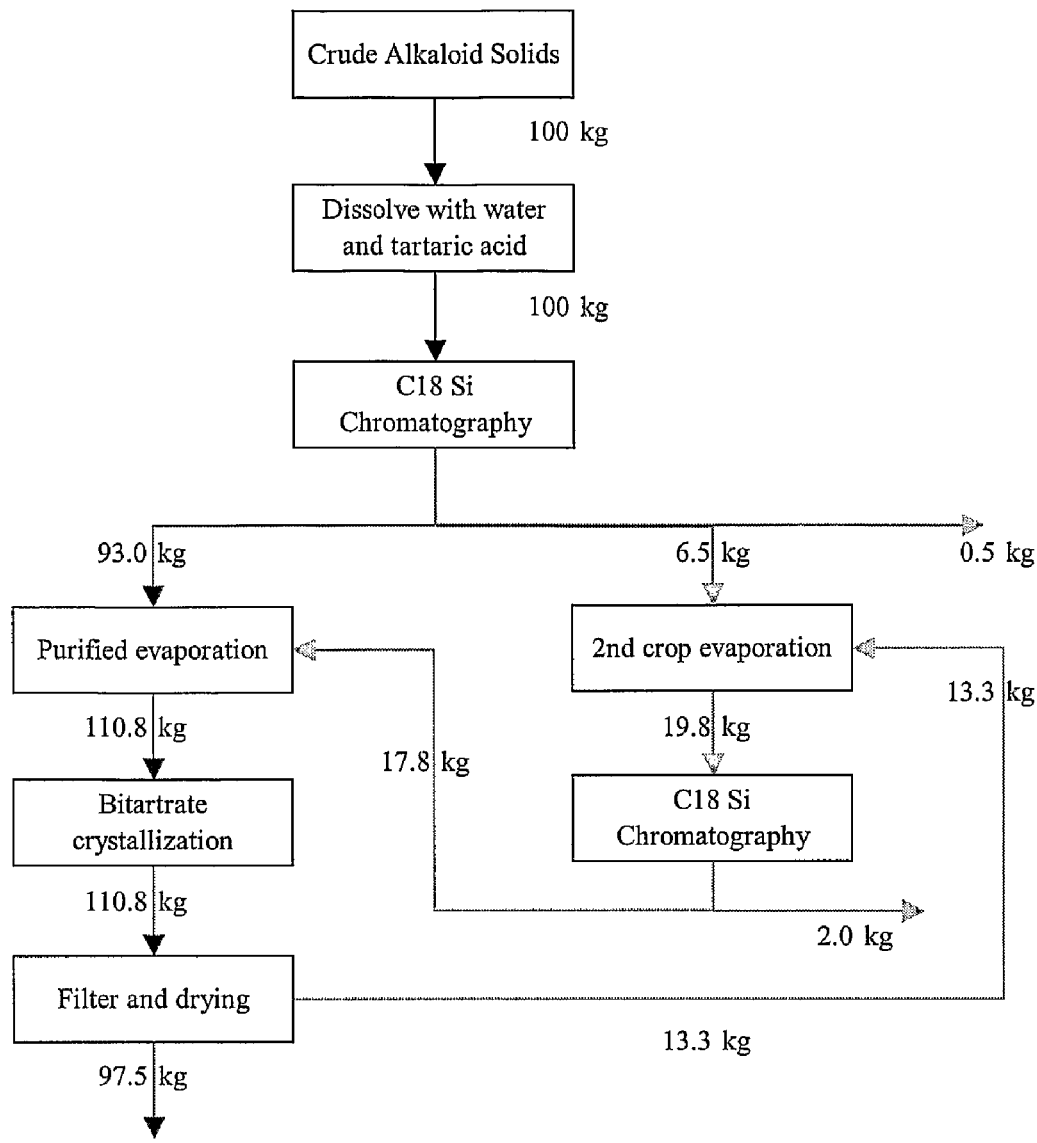
FIG. 1 is a flow chart of a non-limiting illustrative embodiment of the method of the present invention utilizing a crude hydrocodone feed of 100 g.

The process of the present invention is illustrated in FIG. 1. For purposes of this disclosure the following terms are defined:

Area %: A unit of purity calculated from analytical chromatography. It is the area of the desired component divided by the total area detected.

Loading ratio: Mass of stationary phase divided by the mass of alkaloid loaded in purification runs.

Mobile phase: The liquid that is pumped to the column after the feed is loaded. This liquid elutes the components.

Second crop: The alkaloid mass recovered in fractions that require a second pass through the chromatography column. The fractions are concentrated and then purified separately.

Stationary phase: The media that adsorbs the components of the feed to the column.

Yield: The mass of desired component recovered in purified fractions divided by the mass of component fed to the column.

Percent: Unless otherwise noted all percentage amounts stated in this specification and claims are percent by weight.

In one aspect of the present invention, hydrocodone alkaloid is dissolved with water and tartaric acid to form the chromatography feed. The hydrocodone is then purified through the chromatography column. The purified fractions are evaporated to attain the crystallization feed concentration. 3A ethanol (85% ethanol, 10% water, 5% methanol) is added, and the hydrocodone bitartrate is crystallized with cooling. The solids are then dried and milled.

The mother liquor from the crystallization is combined with the impure fractions from the chromatography. This second crop composite is then concentrated in hydrocodone through evaporation. The concentrate is then purified through the chromatography column and apart from any crude hydrocodone base. No impure fractions are recycled in this purification, so that no impurities can accumulate. The purified hydrocodone from the second crop is then combined with the purified material from the first crop in the evaporation step.

The proposed process will have a purification recovery of at least about 95%, preferably at least about 97%. Using the chromatography will allow the α,β unsaturated ketone level to be reduced to less than 10 ppm.

The stationary phase may be one of various materials from the group including but not limited to alkylsilanes, arylsilanes, haloalkylsilanes, alkyl esters, aryl esters, alkyl amines, alkylcyano compounds, alkyldiols, alkyl ethers, aryl ethers, haloalkyl ethers, alkylcarboxylic acids, arylcarboxylic acids, alkysulfonic acids, arylsulfonic acids, polystyrenedivinylbenzene, aminopolycaprolactem and glycidoxyethylmethoxysilzne.

The stationary phase media utilized in an illustrative embodiment is silica with octadecyl-(C18) ligands, although other ligands such as octyl-(C8), butyl-(C4), tricosane-(C23) ligands, cyano or phenyl groups may be employed. The ligands can be attached to other particles such as polymers, zirconium oxide or titanium. The stationary phase is about 1 to about 200 microns, with about 15 to about 50 microns being preferred, and about 20 microns most preferred. In this illustrative embodiment, spherical particles with pores of about 50 to about 300 Å are utilized, with about 90 to about 150 Å being preferred and about 120 Å being most preferred.

A high-performance preparative liquid chromatography column is generally employed. The preparative chromatography column, in an illustrative, non-limiting system, includes a diameter that is about 0.1 to about 200 cm with at least about 5 cm being preferred. The length of the preparative chromatography column is not critical to the process. A preferred length that ranges from about 10 centimeters to about 100 centimeters with a more preferred length that ranges from about 20 centimeters to about 30 centimeters. Even more preferred is a column of about 25 centimeters in length. There are a variety of commercial suppliers that can build preparative chromatography columns of this nature including Amicon, Inc., having a place of business at 72 Cherry Hill Drive, Beverly, Mass. 01915. Amicon, Inc. is the manufacturer of PROCHROM® chromatography columns. Other manufacturers include TechniKrom, Incorporated, having a place of business at 1801 Maple Avenue, Evanston, Ill. 60201, among others. The present invention is applicable to a wide variety of high-performance liquid preparative chromatography columns and is not limited to the specific embodiment detailed in this patent application.

Hydrocodone and its impurities are adsorbed onto the stationary phase and are desorbed, or eluted with a mobile phase containing dilute acid and an organic polar solvent. Suitable acids include but are not limited to acetic, formic, oxalic, lactic, malic, sulfuric, hydrochloric, hydrobromic, phosphoric, phosphorous, and nitric with tartaric being preferred. The organic polar solvent is selected from any number of water soluble, non-interfering solvents such as ethanol, methanol, propanol, isopropanol, butanol, t-butanol and preferably acetonitrile. The aqueous mobile phase is prepared by acidifying water to attain a pH of 1 to 7, with a more preferred pH range of 2 to 3. Typically, the amount of solvent in the aqueous organic solvent solution is in the range of from about 2 percent to about 100 percent. Typically, the amount of organic solvent in the mobile phase increases during the elution process with lower amounts used in the first few passes of mobile phase through the column and then increased amounts are employed to purge the column.

A critical feature of this invention is the Loading Ratio. It has been found that the Loading Ratio employed in the process of this invention is typically in the range of from about 10 to about 1000 grams of media per gram of hydrocodone loaded into the column before the mobile phase is employed. In a preferred illustrative embodiment, the Loading Ratio is in the range of from about 10 to about 40. As is well known, in the analytical use of HPLC the Loading Ratio would be above 10,000 and the feed components would elute in separate peaks. In the preparative chromatography such Loading Ratio would multiply the number of runs in a column by a factor of over 100 or cause the column to be more than 10 times larger diameter. Using the analytical loading conditions would make any new chromatography purification technique impractical, especially at industrial quantities. The feasible preparative application has elution fronts, in which the hydrocodone is collected with the desired purity.

The desired purity obtained in the process of this invention is, of course, in some measure dependent upon the amount of impurities and operating conditions of the chromatographic process. In instances of higher impurities, a Loading Ratio in the higher level of the above noted preferred range would be required. Also, the amount of organic solvent in the mobile phase must be controlled so as not to elute impurities prematurely. As can be seen in the operating examples below those runs with a higher total amount of elution produced higher impurities.

In operation, after the hydrocodone feed solution is loaded into the packed column, the first components are eluted with a mobile phase containing from about 2 to about 10 percent, by weight, organic solvent. As noted above the preferred solvent is acetonitrile. Most of the impurities are collected in a first fraction that is discarded. A second fraction is collected containing an initial, small amount of hydrocodone and the remaining impurities. The second crop will contain about 10 percent of the hydrocodone loaded. The purified hydrocodone is then collected in the third fraction wherein the mobile phase is changed to an increased amount of solvent, in the range of about 8-10 percent, although in some instances the amount of organic solvent in the third fraction can be as high as 15 percent. The third fraction contains about 90 percent of the hydrocodone loaded onto the column. This third fraction is evaporated to remove the solvent and the purified hydrocodone is recovered from solution by precipitation in accordance with standard procedures. A fourth fraction is then obtained to flush the column of the remaining hydrocodone loaded. In the fourth fraction, the aqueous mobile phase employed contains about 50 percent organic solvent, typically acetonitrile. This fourth fraction is then combined with the second fraction and subjected to evaporation to remove the organic solvent. The combined fractions are subjected to the preparative, reverse phase preparative chromatography as described above except that no recycle fractions are collected in order to purge the impurities. The purified, combined second crop is then sent to the precipitation procedure as noted above with respect to the third fraction.

The reverse phase, preparative chromatographic process of this invention is typically operated at a temperature of from about 10° C. to 50° C. with about 20° C. to about 30° C. being preferred. It is noted however that temperature is not critical in this process. Higher or lower temperatures may be employed without significant change in result.

Figure 2:
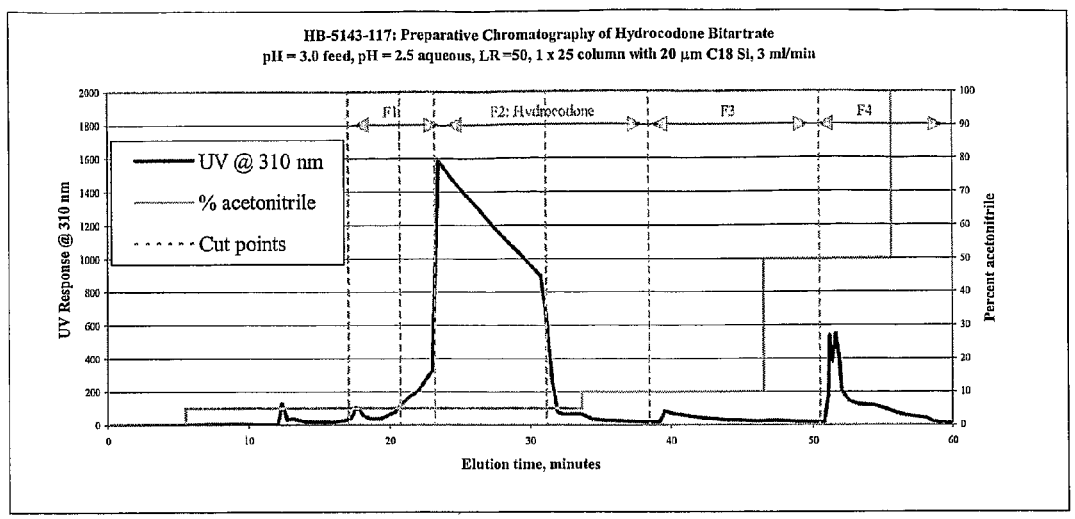
FIG. 2 is a graph indicating the results of a non-limiting illustrative embodiment of a reverse phase, preparative HPLC procedure in accordance with this invention wherein the UV analysis of the product provides an indication of the contents of each fraction of eluant delivered from the column. The Figure also indicates the time; fraction cut lines of each of four fractions and the acetonitrile content of the mobile phase employed in the process.

In operation, it is typical to employ UV analysis of the eluted material from the column. A typical UV profile of eluted material in accordance with the process of this invention appears in FIG. 2. The process producing the UV curve in FIG. 2 employed a feed solution of hydrocodone bitartrate salt at pH 2.5 to a chromatographic column having a dimension of 1×25-cm, with 20 micron particles of silicon having a C18 ligand attached. The Load Ratio was 50 and the flow rate was 3 ml/min. In the Figure, the abscissa denotes elution time in minutes while the left ordinate denotes U absorbance at 310 nm. The right ordinate denotes percent acetonitrile in volume percent in the feed solution. The various fractions collected are denoted as F1-F4. Impurities A and B are consistently occurring peaks denoting uncharacterized impurities.

EXAMPLES

Example 1

Two chromatographic runs were made employing the following conditions:

Objective: Recover hydrocodone with less than 10 ppm a, unsaturated ketone and less than 0.20 area % each Impurity A. B, and C.

Feed Composition: 96.58 area % hydrocodone, 0.23 area % Impurity A, 0.35 area % Impurity C, 0.20 area % Impurity B, 31 ppm $\alpha,\beta$ unsaturated ketone.

Feed pH: 3.00 with tartaric acid
Feed concentration: 28-g/l hydrocodone
Stationary phase: silica with C18 ligands, 20 microns spherical particles with 120-angstrom pores.
Column: 1.0-cm diameter, 25-cm length, and 10.2 g of stationary phase
Flow Rate: 3 ml/min.
Flow direction: top to bottom
Temperature: 25° C.
Detection: 310 nm.
Mobile Phase: dilute tartaric acid solution in water at pH 2.81 and acetonitrile (ACN) added in step gradients of 5 to 75 volume percent.

The results of the first and second trials appear in Table I below.

TABLE I

|  | Trial 1 | Trial 2 |
|---|---|---|
| Loading Ratio | 24 | 16 |
| Area % hydrocodone in purified fraction | 99.92 | 98.54 |
| Area % of Impurity B in purified fraction | 0.08 | 0.21 |
| $\alpha, \beta$ unsaturated ketone ppm in purified fraction | Not detected | Not detected |
| Yield of hydrocodone in purified fraction | 93 | 96 |
| Elution prior to fraction F1 | 30.5 ml of aqueous 13.5 ml of 5% ACN | 56.8 ml of aqueous 1.5 ml 5% ACN |
| Elution of fraction F1 | 12.8 ml of 5% ACN | 5.5 ml of 5% ACN |
| Elution of purified fraction F2 | 46.3 ml of 5% ACN | 74.9 ml of 5% ACN |
| Elution of fraction F3 | 23.6 ml of 5% ACN 31.5 ml of 15% ACN | 32.0 ml or 15% ACN |
| Elution of fraction F4 | 30.0 ml of 75% ACN | 41.5 ml of 75% ACN |

In Trial 1 Impurity B was reduced to less than 0.20 area %, which did not occur in Trial 2. All other impurities were sufficiently reduced. Trial 1 used a loading ratio of 24 g media/g hydrocodone, while Trial 2 loaded too much feed at a ratio of 16. Both trials had nearly the same recovery of hydrocodone in the purified fraction F2, and the remaining hydrocodone was recovered in the F1 and F3 fractions. These fractions were designated as second crop and were to be purified a second time through the column. Trial 2 required a greater volume of F2 to recover the hydrocodone due to the greater feed loading.

Example 2

Objective: Recover hydrocodone with less than 10 ppm α,β unsaturated ketone and less than 0.20 area % each of, Impurity A, B, and C.

Feed composition: 96.58 area % hydrocodone, 0.23 area % Impurity A, 0.35 area % Impurity C, 0.20 area % Impurity B, 31 ppm α,β unsaturated ketone.

Feed concentration: 28 g/l hydrocodone in aqueous solution

Feed pH: 3.00 with tartaric acid

Stationary phase: silica with C18 ligands, 20 μm spherical particles with 120 Å pores.

Column: 1.0 cm diameter, 25 cm length, 10.2 g of stationary phase

Flow Rate: 3 ml/min

Flow direction: top to bottom

Temperature: 25° C.

Detection: 310 nm

Mobile phase: dilute tartaric acid solution in water and ACN. The acetonitrile is added in step gradients of 5-100 volume percent Another pair of trials was made to demonstrate the need to attain desired mobile phase pH. The results of the runs are contained in Table II below.

TABLE II

|  | Trial 3 | Trial 4 |
| --- | --- | --- |
| Loading Ratio | 46 | 41 |
| Mobile phase pH | 2.54 | 3.19 |
| Area % hydrocodone in purified fraction | 99.66 | 99.55 |
| Area % of Impurity C in purified fraction | 0.08 | 0.21 |
| α, β unsaturated ketone ppm in purified fraction | 3 | 31 |
| Yield of hydrocodone in purified fraction | 87 | 70 |
| Elution prior to fraction F1 | 30.0 ml of aqueous 19.5 ml of 5% ACN | 23.0 ml of aqueous 40.0 ml of 5% ACN |
| Elution of fraction F1 | 19.6 ml of 5% ACN | 12.4 ml of 5% ACN |
| Elution of purified fraction F2 | 46.4 ml of 5% ACN | 61.4 ml of 5% ACN 40.0 ml of 10% ACN |
| Elution of fraction F3 | 36.0 ml of 10% ACN | Not taken |
| Elution of fraction F4 | 31.0 ml of 50% ACN | 27.5 ml of 50% ACN 6.0 ml of 100% ACN |

In Table II Trial 3 had the proper mobile phase pH of 2.54. This trial sufficiently reduced all impurities, and 87% of the hydrocodone was recovered in the purified fraction F2. Trial 4 used a higher mobile phase pH of 3.19. This caused a slower elution of the hydrocodone. A lower yield of 70% was collected in F2, which also used 40.0 ml of a 10% ACN flush. The F2 volume was 101.4 ml in Trial 4 compared to 46.6 ml in Trial 3. The lower recovery in Trial 4 also coincided with higher impurity levels for Impurity C and the α,β unsaturated ketone, both of which were above specification.

Example 3

Trials 5 and 6, given in Table III below compare the selection of the media for separation.

Objective: Recover hydrocodone with less than 10 ppm α,β unsaturated ketone and less than 0.20 area % each of Impurity A, B, and C.

Feed composition: 96.58 area % hydrocodone, 0.23 area % Impurity A, 0.35 area % Impurity C, 0.20 area % Impurity B, 31 ppm α,β unsaturated ketone.

Feed concentration: 28 g/l hydrocodone in aqueous solution

Feed pH: 3.00 with tartaric acid

Stationary phase: 20 μm spherical particles with 120 Å pores.

Column: 1.0 cm diameter, 25 cm length, 10.2 g of stationary phase

Flow Rate: 3 ml/min

Flow direction: top to bottom

Temperature: 25° C.

Detection: 310 nm

Mobile phase: dilute tartaric acid solution in water at pH=2.78 and acetonitrile (ACN). The acetonitrile is added in step gradients of 5-75 volume percent

TABLE III

|  | Trial 5 | Trial 6 |
| --- | --- | --- |
| Stationary phase | C18 silica | C8 silica |
| Loading Ratio | 60 | 60 |
| Mobile phase pH | 2.78 | 2.78 |
| Area % hydrocodone in purified fraction | 99.69 | 99.49 |
| Area % of Impurity C in purified fraction | 0.00 | 0.33 |
| Yield of hydrocodone in purified fraction | 90 | 95 |
| Elution prior to fraction F1 | 28.5 ml of aqueous 33.8 ml of 5% ACN | 29.0 ml of aqueous 18.8 ml of 5% ACN |
| Elution of fraction F1 | 12.0 ml of 5% ACN | 4.6 ml of 5% ACN |
| Elution of purified fraction F2 | 37.6 ml of 5% ACN | 32.0 ml of 5% ACN |
| Elution of fraction F3 | 29.3 ml of 5% ACN 43.5 ml of 10% ACN | 24.9 ml of 5% ACN 39.0 ml of 10% ACN |
| Elution of fraction F4 | 23.0 ml of 50% ACN 6.0 ml of 100% ACN | 24.0 ml of 50% ACN |

Trial 5 used the C18 silica and it was able to reduce the levels of Impurities A and B along with Impurity C. Trial 6 used the C8 silica, which was not able to reduce Impurity C to less than 0.20 area %. Both trials were run at the same loading ratio and mobile phase pH. The C8 silica allowed for a quicker arrival of the hydrocodone and a greater recovery in the F2 fraction. Unfortunately, the C8 silica was unable to separate away Impurity C sufficiently.

There has been described a novel process for hydrocodone purification by means of reverse phase, preparative chromatography. While the process of this invention has been described with reference to specific compounds and examples, no intention is made by such reference to limit the scope of this invention unless expressly stated. Various modifications may be made in the materials and sequence of process steps as well as process combinations, which are adapted to suit the various process steps without departing from this invention. The foregoing description is given for clarity of understanding only and no unnecessary limitations should be understood there from, as modifications will be obvious to those skilled in the art.

What is claimed is:

1. A process for recovering hydrocodone from a hydrocodone preparation, the process comprising subjecting the hydrocodone preparation to reverse-phase liquid chromatography wherein the loading ratio of a stationary phase to hydrocodone is not more than about 1000, and wherein the hydrocodone recovered is at least about 95% pure.

2. A process for recovering hydrocodone from a hydrocodone preparation which comprises subjecting the hydrocodone preparation to a reverse-phase high performance preparative liquid chromatography and recovering hydrocodone.

3. The process of claim 1 wherein the loading ratio is in the range of about 10 to about 1000.

4. The process of claim 1 wherein the loading ratio is in the range of about 20 to about 40.

5. The process of claim 1 wherein the stationary phase is selected from the group consisting of alkylsilanes, arylsilanes, haloalkylsilanes, alkyl esters, aryl esters, alkyl amines, alkylcyano compounds, alkyldiols, alkyl ethers, aryl ethers, haloalkyl ethers, alkylcarboxylic acids, arylcarboxylic acids, alkysulfonic acids, arylsulfonic acids, polystyrenedivinylbenzene, aminopolycaprolactam and glvcidoxyethylmethoxysilane.

6. The process of claim 1 wherein the stationary phase is a bonded-phase silica containing ligands selected from the group consisting of butyl-, octyl-, octadecyl-, tricosane-, cyano- and phenyl-moieties.

7. The process of claim 6 wherein the ligand is octadecylsilane.

8. The process of claim 1 wherein a chromatography column is eluted with a mobile phase comprising an aqueous acidic solution containing an organic solvent.

9. The process of claim 8 wherein the acid employed to acidify the aqueous acidic solution is selected from the group consisting of acetic, malic, tartaric, sulfuric, formic, oxalic, lactic, hydrochloric, hydrobromic, phosphoric, phosphorous, and nitric.

10. The process of claim 8 wherein the aqueous mobile phase pH is in the range of from about 1 to about 7.

11. The process of claim 10 wherein the pH is in the range of from about 2 to about 3.

12. The process of claim 8 wherein the organic solvent is an alcohol.

13. The process of claim 12 wherein the alcohol is selected from the group consisting of methanol, propanol, isopropanol, butanol and t-butanol.

14. The process of claim 8 wherein the organic solvent is acetonitrile.

15. The process of claim 1 wherein the hydrocodone preparation is acidified so as to prepare a hydrocodone salt.

16. The process of claim 15 wherein the acid employed to acidify the hydrocodone preparation is an inorganic acid.

17. The process of claim 16 wherein the inorganic acid is selected from the group consisting of, sulfuric acid hydrochloric acid, hydrobromic acid, phosphoric acid, phosphorous acid, and nitric acid.

18. The process of claim 15 wherein the acid employed to acidify the hydrocodone preparation is an organic acid.

19. The process of claim 18 wherein the organic acid is selected from the group consisting of acetic acid, malic acid, tartaric acid, formic acid, oxalic acid, and lactic acid.

20. The process of claim 15 wherein the pH of the hydrocodone preparation is in the range of from about 1 to about 7.

21. The process of claim 20 wherein the pH of the hydrocodone preparation is in the range of about from about 2 to about 3.

22. The process of claim 17 wherein the organic acid is tartaric acid.

23. The process of claim 14 wherein the acetonitrile is in the range of from about 5 to about 100 volume percent.

24. The process of claim 14 where the acetonitrile is in the range of from about 2 to about 20 volume percent during the collection of the purified hydrocodone.

25. A process for purifying a hydrocodone preparation containing an $\alpha,\beta$ unsaturated ketone, the process comprising the steps of
(a) packing a chromatographic column with a reverse-phase chromatographic packing material;
(b) passing through said column an aqueous, acidified solution of hydrocodone preparation at a loading ratio of from about 10 to about 1000 and
(c) eluting said column with an aqueous solution of an organic solvent to produce an eluate containing hydrocodone having less than about 10 ppm $\alpha,\beta$ unsaturated ketone.

26. The process of claim 25 wherein the eluate is divided into four fractions wherein:
(i.) a first fraction is discarded,
(ii.) a second fraction that is combined with a fourth fraction wherein the water and organic solvent are substantially reduced and then recycled through the column, and
(iii.) a third fractions that contains less than about 10 ppm $\alpha,\beta$ unsaturated ketone.

27. The process of claim 1, wherein the reverse-phase liquid chromatography comprises a reverse-phase high performance preparative liquid chromatography.

28. The process of claim 7, wherein a chromatography column containing the stationary phase is eluted with a mobile phase comprising an aqueous acidic solution containing acetonitrile.

* * * * *